United States Patent
Lelah

(10) Patent No.: US 11,446,305 B2
(45) Date of Patent: Sep. 20, 2022

(54) COMPOSITION AND METHOD TO ENHANCE PERFORMANCE FOR ELECTRONIC VIDEO GAME PLAY

(71) Applicant: NutriScience Innovations LLC, Milford, CT (US)

(72) Inventor: Michael Lelah, Chicago, IL (US)

(73) Assignee: NutriScience Innovations LLC, Milford, CT (US)

( * ) Notice: Subject to any disclaimer, the term of this patent is extended or adjusted under 35 U.S.C. 154(b) by 0 days.

(21) Appl. No.: 16/707,921

(22) Filed: Dec. 9, 2019

(65) Prior Publication Data

US 2021/0169891 A1    Jun. 10, 2021

(51) Int. Cl.
| | | |
|---|---|---|
| *A61K 36/00* | (2006.01) | |
| *A61K 31/522* | (2006.01) | |
| *A61K 31/197* | (2006.01) | |
| *A61K 31/14* | (2006.01) | |
| *A61P 25/28* | (2006.01) | |
| *A61K 31/198* | (2006.01) | |
| *A61K 31/194* | (2006.01) | |
| *A61K 36/81* | (2006.01) | |
| *A61K 31/05* | (2006.01) | |

(52) U.S. Cl.
CPC ............ *A61K 31/522* (2013.01); *A61K 31/05* (2013.01); *A61K 31/14* (2013.01); *A61K 31/194* (2013.01); *A61K 31/197* (2013.01); *A61K 31/198* (2013.01); *A61K 36/81* (2013.01); *A61P 25/28* (2018.01)

(58) Field of Classification Search
CPC ..................................................... A61K 36/00
USPC .......................................................... 424/725
See application file for complete search history.

(56) References Cited

U.S. PATENT DOCUMENTS

2008/0206340 A1*   8/2008   Hefel ..................... A61P 43/00
                                                                424/488

* cited by examiner

*Primary Examiner* — Michael V Meller
(74) *Attorney, Agent, or Firm* — Stephen T. Scherrer; Monique A. Morneault; Scherrer Patent & Trademark Law, P.C.

(57) ABSTRACT

The present disclosure relates to relates to improved dietary supplement compositions formulated in a therapeutic effective amount for enhancing play of electronic video games. Specifically, the present disclosure relates to compositions for oral consumption, in the form of dietary supplements, foods or beverages, which provide fast acting, broad spectrum cognitive enhancing formulas for gaming and video game purposes. The formulas consist of ingredients for enhancing certain parameters to improve gaming abilities, including increased energy and alertness, brain wave function, neurotransmission, reduced stress, improved sleep, improved eye health, improved blood flow, and improved hydration and reduced muscle soreness.

1 Claim, No Drawings

COMPOSITION AND METHOD TO ENHANCE PERFORMANCE FOR ELECTRONIC VIDEO GAME PLAY

TECHNICAL FIELD

The present disclosure relates to compositions and method for enhancing game play of electronic video games. Specifically, the present disclosure relates to dietary and nutritional supplement compositions and methods to provide fast acting, broad spectrum cognitive enhancing formulas for gaming and video game purposes.

BACKGROUND

A video game is an electronic game that involves interaction with a user interface to generate visual feedback on a two- or three-dimensional video display device such as a TV screen, virtual reality headset, computer monitor, mobile device or virtual reality system or other system. Video games may be designed or played for entertainment, education, casual fun, or serious sport (esports). Video games may be designed or played by a single player or may be linked together through a virtual or hard-wired network to be played by multiple players or multiple teams simultaneously. eSports (also known as e-sports, Esports, or electronic sports) is a form of competition using video games. Most commonly, eSports involves organized, multiplayer video game competitions, particularly between professional players, individually or as teams. Although organized online and offline competitions have long been a part of video game culture, these started largely between amateurs but now have evolved to include participation by professional gamers and spectatorship in these events through live streaming which has resulted in a large surge in popularity. eSports is a significant factor in the video game industry, with many game developers actively designing toward a professional eSports subculture. Common eSport genres are multiplayer online battle arena (MOBA), first person shooter (FPS), fighting, digital collectable card games, battle royale games, and real time strategy (RTS). There are a number of tournaments such as the League of Legends World Championship, Dota 2's The International, the fighting games-specific Evolution Championship Series (EVO), and the Intel Extreme Masters where players and teams compete for prizes.

Serious gaming places tremendous demand on many aspects of cognition and vision at the same time. On an otherwise level playing field, brain function can ultimately determine gaming success. During high intensity gameplay, fluid and fast reaction give gamers an edge. Gaming requires significant and taxing cognitive abilities, such as heavy cognitive workload, visuospatial skills to help perceive, recognize, and manipulate visual stimuli, enhanced attention span, focus and attention, working memory, mental energy, stress resistance, tactile control, hand-eye coordination, resistance to distraction, peripheral vision, analytical skills, spatial skills, problem solving skills, flexibility, adaptability, strategic thinking, and creativity.

In order to improve these cognitive skills, training is part of any serious eSport-type activity. Enhanced cognitive abilities can be developed through simulations and other training programs.

However, as with any physical sport, players will use performance-enhancing drugs to enhance performance. Stimulants, such as Ritalin®, Adderall® and Vyvanse® can significantly boost concentration, improve reaction time and reduce fatigue. Conversely, calming drugs such as propranolol and Valium® can help remain calm under pressure. These drugs can pose severe risks to players because of side-effects, such as addiction and overdose. Additionally, many of the eSport organizations are moving towards banning drugs which fall under WADA (World Anti-Doping Federation). Such drugs are banned, and their use could lead to penalties and expulsion.

The alternative to the legal and illegal use of drugs is the use of legal dietary or nutritional supplements and nutritional foods and beverages. Brain-boosting nootropic supplements, foods and beverages can enhance several cognitive functions to promote a state of peak gaming performance. Brain-boosting, cognitive health and nootropic dietary supplements and safe, legal and effective for both recreational and professional gaming use.

Many such supplement, food and beverage cognitive products are available on the market; they are not specifically designed for gaming use. One problem is that most of these supplements take too long to be effective. Many require 45-60 days for clinical effects to be observed. Gamers require fast acting performance enhancing dietary supplements. Most of the cognitive supplements available do not meet this critical requirement for gamers. Typically, formulas consisting of vitamins and minerals are not effective for short term enhancement. Additionally, gamers require multiple different cognitive abilities, as described above. A simple cognitive formula will not provide such improvements across multiple aspects of cognitive performance. What is needed is a fast acting, broad spectrum cognitive dietary supplement formula, which can be consumed either as a pill (capsule, tablet, softgel, chewable, lozenge, etc), powder for use in a drink or shake, ready to drink (RTD) beverage, or as a food, among other similar formats. Broad spectrum means the use of multiple ingredients in the formula in order to provide enhanced cognitive performance across many aspects and skills critical to gamers.

A need, therefore, exists for an improved dietary supplement composition formulated in a therapeutic effective amount to enhance performance for gaming or video gaming purposes. Specifically, a need exists for an improved dietary supplement composition formulated in a therapeutic effective amount to increase energy and alertness, brain wave function, neurotransmission, reduced stress, improve sleep, improve eye health, improve blood flow, and improve hydration and reduce muscle soreness.

Moreover, a need exists for an improved dietary supplement composition formulated in a therapeutic effective amount to enhance, improve and support multiple aspects of cognitive skills during extended video game play.

A need further exists for an improved dietary supplement composition formulated in a therapeutic effective amount to immediately enhance, improve and support multiple aspects of cognitive skills during extended video game play.

A need further exists for an improved dietary supplement composition formulated in a therapeutic effective amount offering a sustained release to enhance, improve and support multiple aspects of cognitive skills during extended video game play.

A need further exists for an improved dietary supplement composition formulated in a therapeutic effective amount to enhance, improve and support multiple aspects of cognitive skills during extended video game play without negative side effects.

SUMMARY

The present disclosure relates to improved dietary supplement compositions formulated in a therapeutic effective amount for enhancing play of electronic video games. Specifically, the present disclosure relates to compositions for oral consumption, in the form of dietary supplements, foods or beverages, which provide fast acting, broad spectrum cognitive enhancing formulas for gaming and video game purposes. The formulas consist of ingredients for increasing energy and alertness, brain wave function, neurotransmission, reduced stress, improved sleep, improved eye health, improved blood flow, and improved hydration and reduced muscle soreness.

To this end, in an embodiment of the present disclosure, an improved dietary supplement composition formulated in a therapeutic effective amount to enhance performance for gaming or video gaming purposes, is provided. The compositions comprise, in therapeutically effective amounts, various combinations of the following ingredients: caffeine, L-theanine, a choline bitartrate, an adaptogen, lutein, and zeaxanthin, with or without L-arginine, potassium salt, L-malic acid, and betaine.

In one embodiment of the present disclosure, an improved dietary supplement composition is provided having the following ingredients: Innovatea®, a natural source caffeine, Suntheanine®, an enzymatically sourced L-theanine, choline bitartrate, Shoden®, an ashwagandha extract standardized to 35% glycowithanolides, Xanmax® lutein and zeaxanthin, L-arginine, NuMalic™ L-malic acid, Coco-K™ potassium-containing coconut powder and betaine.

In one embodiment, a dietary supplement composition is provided, wherein the composition comprises: 75-150 mg natural caffeine, 50-200 mg L-theanine, 100-500 mg choline bitartrate, 60 mg-600 mg ashwagandha extract, 100 mg combination of 10 mg lutein and 4 mg zeaxanthin, 500-1,000 mg L-arginine, 1,000 mg potassium, 500 mg L-malic acid, and 2,500 mg betaine.

In one embodiment, a dietary supplement composition is provided, wherein the composition comprises: 75-150 mg natural caffeine, 50-200 mg L-theanine, 100-500 mg choline bitartrate, 60 mg-600 mg ashwagandha extract, 100 mg combination of 10 mg lutein and 4 mg zeaxanthin.

In another embodiment, an improved dietary supplement composition formulated in a therapeutic effective amount to enhance performance for gaming or video gaming purposes, is provided, wherein the formulation has an immediate effect on enhancing performance to the player.

In another embodiment, an improved dietary supplement composition formulated in a therapeutic effective amount to enhance performance for gaming or video gaming purposes, is provided, wherein the formulation has a delayed release effect providing synergistic effects within an extended period of time for continuous play, even over several days.

In yet another embodiment, a dietary supplement composition formulated in a therapeutic effective amount to enhance performance for players during gaming or video gaming, is provided, wherein the composition comprises a first composition comprising caffeine, L-theanine, choline bitartrate, ashwagandha and lutein/zeaxanthin, a second composition comprising L-arginine, potassium salt, L-malic acid, and betaine, wherein the first composition and the second composition are consumed separately in a single dosage combination.

It is, therefore, an advantage and objective of the present disclosure to provide an improved dietary supplement composition formulated in a therapeutic effective amount to enhance performance of a player without negative side effects.

Additional features and advantages of the present invention are described in, and will be apparent from, the detailed description of the presently preferred embodiments and from the drawings.

DETAILED DESCRIPTION

The present disclosure relates to an improved dietary supplement composition formulated in a therapeutic effective amount to enhance performance for gaming or video gaming purposes. The present disclosure relates to providing a formula for oral consumption, in the form of a dietary supplement, food or beverage, which provides a fast acting, broad spectrum cognitive enhancing formula for gaming and video game purposes. The ingredients used in the present composition are food or dietary ingredients, and do not include chemicals or drugs that are not suitable for human consumption as foods or dietary supplements. The aspects of this set of formulas which distinguish them from all other formulas are the fast-acting nature of the ingredients, and the broad spectrum of their action on cognitive activity.

It is a key embodiment of the present disclosure that the broad-spectrum compositions consist of dietary ingredients which have fast acting simultaneous positive effects on energy and alertness, brain wave function, vision, cognitive, brain or nootropic functionality, neurotransmitter enhancement, sleep, calming, blood flow enhancement, hydration and reduced muscle soreness. It is these particular functionalities that make the present dietary supplement composition unique. For example, it is non-obvious that such a composition contains ingredients that both increase energy and alertness, yet at the same time enhance sleep and calmness. Additionally, it is a unique feature of the present composition to include ingredients that improve brain wave function, a physical manifestation of improved cognitive function, as well as improve neurotransmission, a chemical manifestation of improved cognitive function.

In traditional neurobiological analysis, it is the chemical or biochemical activities that predetermines brain wave function. It is a non-obvious aspect of the present composition that there is a synergistic and interactive effect with mutual feedback, of combining neurotransmission and brain wave enhancement. The present composition is not just directed to improving neurotransmission, which improves brain wave function, but at the same time improving brain wave function improves neurotransmission. This leads to a synergistic and interactive effect of combining ingredients which affect body systems in this fashion. This unique embodiment of the present composition is critical for gamers and enhancement of video gaming cognitive capabilities.

Another feature of the present dietary supplement composition is the creation of a formula with fast acting ingredients. Gamers and video game players need to have fast improvement in cognitive and other functions. For the purposes of this disclosure, "fast" is defined as having an effect within 30-60 minutes, but can also be defined as acting within a few days. In a novel embodiment the formulas created in this invention have two periods of effect—very fast (30-60 minutes) for immediate effect during gaming, and fast (1-5 days) for synergistic effects, which manifest themselves within a short enough period so that users will continue to use and consume the formula for a few days in order to experience effects.

If an enhanced effect is not observed within a few days, gamers will generally give up consuming the supplement and move on to some other product. Not fast, or slow effect is defined as having an effect after at least 2 weeks and more likely within 45-60 days. Gamers need fast effect, and this precludes most of the cognitive, brain and nootropic dietary supplement formulas that have been created and are available on the market today. Most of these cognitive formulas are designed for long term cognitive improvement, with the aim to forestall dementia and other neurodegenerative diseases, to improve long term memory, to prevent the long-term decline in cognitive function, etc. These are not of interest to gamers and are not the focus of this disclosure.

The present disclosure relates to a novel dietary supplement, food or beverage formula which consists of a functional ingredient or combination of ingredients for use by gamers, including video gamers, which may do one or more of the following: increase energy and alertness, increase brain wave function, improve neurotransmission, improve sleep and calm, improve vision, improve blood flow, improve hydration and/or reduce muscle soreness. A single ingredient may improve one or more of these functionalities. Additionally, a combination of ingredients may improve one or more of these functionalities.

For example, a fast-acting ingredient which increases energy and alertness is caffeine. Caffeine is well-known to increase energy and alertness. However, for enhancing alertness, caffeine is typically used in dietary supplements, foods and beverages at levels of 200 to 400 mg per serving. For gamers however, these high levels of caffeine can cause jitteriness and have unintended side effects that can actually reduce the positive effects of caffeine. In the present composition, a dose of about 75 mg is expected to provide a suitable dose of caffeine to increase energy and alertness but at the same time avoid potential negative side effects. Additionally, when caffeine is combined with another ingredient of the present composition, L-theanine, the L-theanine helps moderate the negative effects of caffeine and is a critical component of a caffeine-containing formula for gamers.

In the present disclosure, the type of caffeine chosen is specifically naturally extracted caffeine. Most of the caffeine on the market is synthetic caffeine. However, there are two sources of natural caffeine—from tea and from coffee. Innovatea® is a 98% pure caffeine extracted from tea leaves, and is preferably the source of caffeine for the present composition. Conventional wisdom is that there is no difference between synthetic caffeine and natural caffeine. This is based on chemical analysis which shows that the chemical form of synthetic caffeine is identical to the natural form. However, in connection with the present composition, there are surprising differences between synthetic and natural caffeine, which affect gamer performance. For example, when dissolved in water, it has been found that synthetic caffeine is much harsher to the taste than natural caffeine. Taste is an important psychological contributor to cognitive function. Therefore, it is an additional feature of the present disclosure that natural-source caffeine will have an enhanced effect on cognitive performance than will synthetic caffeine because it is more palatable.

Another component of the present composition, L-theanine, is a non-essential amino acid which affects brain wave function. L-theanine is fast-acting. In 30-60 minutes, L-theanine increases desirable brain alpha-wave activity and reduces undesirable brain beta-wave and theta-wave activity. L-theanine is a critical ingredient in the gamer formula because of its effects on the physical aspects of cognitive improvement. As another function of L-theanine, L-theanine is known to moderate the negative effects of caffeine, like jitteriness, which is a negative side effect of consuming caffeine for gamers who need all their motor skills available to them during playing video games. L-theanine. There is therefore a synergistic effect of combining L-theanine with caffeine in a fast-acting gamer formula.

For the present composition, there are two sources of L-theanine—L-theanine may be produced by chemical synthesis, or by enzymatic fermentation. Although the chemical structure of L-theanine in both cases is the same, there are differences in other properties of the two forms of L-theanine. A solution of synthetic L-theanine in water tastes slightly astringent, while a solution of enzymatically produced L-theanine in water tastes mild. Similar to the taste of caffeine, this difference in taste affects cognitive function and the mild tasting enzymatically produced L-theanine is an unexpected effect and is the preferred component. For example, Suntheanine® is enzymatically produced L-theanine. The dose of Suntheanine® is between 50 and 200 mg per serving, with a preferred dose of 50-100 mg. At this dose range, the effects of Suntheanine® on brain alpha-wave production have been previously established.

Another ingredient of the present composition is a neurotransmitter agent which affects acetylcholine biochemistry in the brain and is a required component of the formula. Choline is a precursor to acetylcholine. The concept here is to flood the body with choline, which then maximizes the activity and regeneration of acetylcholine. It is known for example that marathon runners deplete choline during a marathon. This effect of intense physical activity causing a depletion of choline in the body is extended to the present composition to intense mental activity during gaming, which is also depleting choline in the body. This is an unexpected effect because there is no known direct connection between the amount of choline in the body and the intensity of mental exercise.

There are many different forms of choline which can be used, for example choline bitartrate and phosphatidyl choline. Choline bitartrate is a soluble form of choline and is a more preferred form. Choline bitartrate is highly bioavailable and acts rapidly to increase choline levels in the blood. Another aspect of the present disclosure is the synergistic combination of L-theanine and choline bitartrate, where the L-theanine effects on brain waves and the choline bitartrate effects on the acetylcholine neurotransmitter are expected to be synergistic and mutually interactive with mutual feedback as previously discussed. In the present disclosure, the dose of choline bitartrate, which contains 40% choline is between 30 and 550 mg choline (550 mg choline is the Daily Value) which is between 75 mg and 1,375 mg choline bitartrate. In a preferred embodiment, the amount of choline bitartrate is between 75 and 500 mg choline bitartrate (delivers 30-200 mg choline).

Yet another ingredient of the present composition is an adaptogen, which improves brain health, reduces stress and anxiety, increases calm and relaxation, improves sleep ability, restores balance, and improves physical performance. An adaptogen is an herb that has hormonal activity and protects the body against stress and other insults. Adaptogens are also known as phytohormones—i.e., plant extracts with hormonal-like activity. A hormonal-like ingredient is a necessary component of the gamer formula as hormonal action is critical to improved gamer performance. Adaptogens include but are not limited to rhodiola and ashwagandha. Ashwagandha is a preferred adaptogen. Ashwagandha has the unique ability to help maintain homeostasis during intense stress, which is exactly what is needed by gamers to balance their performance. Ashwagandha is an Indian Ayurvedic herb also known as Indian ginseng, poison gooseberry, or winter cherry, and is also known by its Latin name *Withania somnifera*. Ashwagandha extract containing at least 5% withanolides (the bioactive components of Ashwagandha) is more preferred with at least 35% glycowithanolides even more preferred. Preferred dosages for ashwagandha extract are between 60 mg and 600 mg, with more preferred dosages between 60 and 300 mg, with further preferred dosages between 60 and 120 mg per day. Ashwagandha extract bioavailability is high and effects can be felt within a few days making it a suitable selection for a fast-acting component of the formula in this composition.

In another ingredient in the present composition is a combination of fast-acting eye health ingredients, which provides a novel synergistic combination with the other cognitive ingredients to provide a unique and broad-spectrum gamer formula. There are many suitable eye health ingredients including lutein (free and ester forms), zeaxanthin, astaxanthin, beta-carotene and other carotenoids. In a preferred embodiment, a combination of free lutein and zeaxanthin is used. In a more preferred embodiment, free lutein and zeaxanthin in the ratio of 20:4 is preferred, with 10 mg free lutein and 2 mg zeaxanthin as the more preferred dose. Most preferred is 100 mg Xanmax® free lutein and zeaxanthin which contains 10 mg lutein and 4 mg zeaxanthin. This combination was included in the AREDS 2 (National Institute of Health, Age-Related Eye Disease Study 2) study and is highly bioavailable. In addition, there is new evidence that lutein plays a role in cognitive improvement as therefore will work synergistically in the present formula.

A further ingredient in the present composition is a dietary ingredient, which helps increase blood flow. Enhanced blood flow helps in several aspects of gaming. Increased blood flow generally increases energy and attentiveness. Increased cerebral (brain) blood flow enhances cognitive function. Enhanced blood flow to the extremities improves tactile capabilities. These synergistic effects with other ingredients in the gamer formula are unique. There are many suitable dietary ingredients for enhancing blood flow including L-arginine and pine bark extract. A preferred dietary ingredient for rapidly enhancing blood flow is L-arginine. A preferred dose is 500-1200 mg per day. A more preferred dose is 500 mg per day.

Yet another ingredient in the present composition is a dietary ingredient, which increases hydration and reduces muscle cramps. Being hydrated is critical to enhanced gamer performance. As an aside, consumption of alcohol reduces hydration and is not generally recommended to be taken with gamer formulas. The synergistic effects of reduced hydration and reduced propensity for muscle cramps enhances peak performance during gaming. There are many suitable dietary ingredients which increase hydration and reduce muscle cramps. Potassium containing dietary ingredients including NutriGP™ potassium glycerophosphate, potassium chloride, and Coco-K™ coconut water powder containing natural potassium are preferred ingredients. Potassium ion is fast acting. Betaine sugar beet extract increases hydration and reduces muscle soreness. NuMalic™ L-malic acid reduces muscle soreness. NutriGL™ potassium glycerophosphate (also known as potassium glycerol 3-phosphate), Coco-K™ potassium-containing coconut powder and betaine sugar beet extract are preferred ingredients in the present gamer formula. Elemental potassium levels should be 99 mg per day as provided by NutriGL™ potassium glycerophosphate or Coco-K™ potassium-containing coconut powder. Betaine sugar beet extract (also known as trimethylglycine) is also a synergistic nootropic which enhances the production of SAMe in the body. SAMe produces dopamine and serotonin—hormones which enhance cognitive function. Betaine dosages are preferred at 2.5-5 grams per day; the more preferred dose is 2.5 grams per day.

The present dietary supplement composition can be in any suitable delivery form including pills (capsules, tablets, softgels, lozenges, chewables) gummies, powders for mixing to form beverages, ready to drink (RTD) beverages, or in foods such a snack bars, cookies or other food forms. In order to formulate these forms of oral consumables, there typically is the need to include inert ingredients. Inert ingredients do not perform any biological function, but instead help create the final form of the product suitable for consumption. Types of inert ingredients include fillers, coatings, lubrication aids, flow agents, binders, preservatives, flavors, fragrances, viscosity modifiers etc. The final product supplement, food or beverage may include any or all of these excipients as necessary to form the product, and it should be noted are not limited to these items listed.

Alternatively, the present dietary supplement composition may be the form of a sustained release or delayed release product in order to prolong the effects of the formula for the player. Some games may last many hours and for a sustained effect of the formula, it is desirable to have a sustained release formula. Sustained release means the release of the ingredient from the formula over a period of about 8-24 hours, with preferred release of 8-12 hours. It may also be desirable to delay release certain ingredients such as caffeine, which may be necessary to perk up the player after many grueling hours. Delayed release means the release of the ingredient in the formula of 2-6 hours with preferred release 2-4 hours. Sustained release and/or delayed release forms may include delayed release or enteric coated capsules or other forms of sustained release beadlets or formulas, without limit.

Although the present dietary supplement composition should ideally include most if not all the different components discussed above, some of these ingredients can to be taken separately, for example, as a separate pill and powder combination. For example, in one embodiment the dietary supplement composition may be provided in a pill form, contain specific ingredients, which is taken together with a powder in the form of a powdered drink containing another set of ingredients. The pill generally includes ingredients that are consumed in small quantities, which are easily produced as a pill and/or may be too astringent to consume as a powder. The powder would include the other ingredients that are generally included in larger quantities in the formulas. For example, preferred amount of these ingredients in the powder portion of the formula and providing a unique synergistic combination include: L-arginine 1,000 mg per day, NuMalic™ L-malic acid 500 mg per day, Coco-K™ potassium-containing coconut water 1,000 mg per day and betaine sugar beet extract 2,500 mg per day.

EXAMPLES

The following are an explanation and results of usage trials utilizing combinations of the above ingredients in a dietary supplement useful for enhancing performance for gaming, including video gaming. Studies were conducted to evaluate the effectiveness and performance enhancing features of the following formulations:

Trial 1. A dietary supplement formulation (Formula 1) was prepared having the following: 75 mg Innovatea® natural caffeine, 75 mg enzymatically produced Suntheanine® L-theanine, 100 mg choline bitartrate, 120 mg Shoden® ashwagandha extract containing 35% glycowithanolides, 100 mg Xanmax® 2004 eye formula containing 10 mg lutein and 2 mg zeaxanthin. Formula 1 was prepared in a single gelatin capsule; multiple capsules were prepared for the trial.

Trial 2. A dietary supplement formulation (Formula 2) was prepared having the following: 150 mg Innovatea® natural caffeine, 150 mg enzymatically produced Suntheanine® L-theanine, 500 mg choline bitartrate, 120 mg Shoden® ashwagandha extract containing 35% glycowithanolides, 100 mg Xanmax® 2004 eye formula containing 10 mg lutein and 2 mg zeaxanthin. Formula 2 was prepared by dividing the formulation evenly into two gelatin capsules, so that the subjects consumed two capsules for a full dosage.

Trial 3. A dietary supplement formulation in a powder form (Formula 3) was prepared having the following: 1,000 mg L-arginine, 500 mg NuMalic™ L-malic acid, 1,000 mg Coco-K™ potassium-containing coconut water containing 100 mg elemental potassium and 2,500 mg betaine sugar beet extract. Trial 3 consists of combining this formula in powder form (Formula 3) with the two capsules of Formula 2. The powder and capsules were consumed separately but at the same time by the subjects. Multiple samples were prepared for the trial.

In each of these trials, 3 male and 2 female volunteer subjects between 25 and 35 years old who are active video gamers were instructed to consume the specific trial formula for 3 days, one sample each day. The volunteer subjects signed Informed Consent forms and completed a questionnaire prior to starting each trial and the same questionnaire at the end of each trial. The subjects completed the questionnaire immediately after completing ½ hour of gaming. All volunteer participants were informed of the total list of ingredients in all 3 formulas but were not told the quantities or the specific ingredients in each formula.

The questionnaire consisted of about 25 questions separated into the following 6 groups of parameters: (a) general questions about health and participation in the trial; (b) specific questions related to memory/recall, mental ability speed, screen vision, mechanical reflexes, finger movement, and energy level; (c) questions related to sleep quality, refresh and tiredness; (d) performance questions related to gaming performance, skills and scores; (e) strategic thinking, and; (f) adverse events related to stomach, brain/headache, physical (muscle/skeletal), vision and other. Scoring was between 1 and 5 with 1 being best and 5 being worst. All scoring was based on volunteer subject self-assessments. All the answers to the questions were tabulated and averaged.

The results of the trials show no adverse events, either physical or mental, from consuming the supplements were noted. All participants completed the trials without any issues. There was no obvious difference between male and female responses and further analysis by gender was not undertaken.

Results from Trial 1: In Trial 1, 5 volunteer subjects consumed Formula 1 for 3 days (1 capsule each day) and completed a questionnaire prior to consuming the capsule and after completing ½ hour of gaming (baseline), and then again at the end of day 3 after completing ½ hour of gaming. Thirteen parameters were tested, including: memory/recall, mental ability speed, screen vision, mechanical reflexes, finger movement, energy level, sleep quality, refreshed, tiredness, overall gaming performance, overall gaming skills, overall gaming scores, and strategic thinking. Comparing results at the beginning and then at the end of the trial, average scores for all 13 parameters studied improved 21.5% over baseline. The greatest improvements in scores (>33.3%) were recorded for energy level, overall gaming performance, and strategic thinking. All specific gaming parameters (including memory/recall, mental ability speed, screen vision, mechanical reflexes and finger movement) showed improvements in score. No gaming parameters decreased. Quality of sleep scores improved slightly.

Results from Trial 2: In Trial 2, 5 volunteer subjects consumed Formula 2 for 3 days (2 capsules each day) and completed a questionnaire prior to consuming the capsules and after completing ½ hour of gaming (baseline), and then again at the end of day 3 after completing ½ hour of gaming. Comparing results at the beginning and then at the end of the trial, average scores for all 13 parameters studied improved 14.5% over baseline. All gaming scores showed improvements in score after consuming the capsules. No gaming parameters decreased. The smaller improvement in scores for Trial 2 can be explained on the basis that Trial 2 was undertaken at the completion of Trial 1 and thus the improvements likely reflected the smaller increases in formula composition.

Results from Trial 3: In Trial 3, 5 volunteer subjects consumed a combination of Formulas 2 and 3 for 3 days (2 capsules and one powder formula each day) and completed a questionnaire prior to consuming the formulas and after completing ½ hour of gaming (baseline), and then again at the end of day 3 after completing ½ hour of gaming. Comparing results at the beginning and then at the end of the trial, average scores for all 13 parameters studied improved 27.2% over baseline. The greatest improvements in scores (>33.3%) were recorded for mental ability speed, screen vision, finger movement, energy level, and gaming scores. All gaming scores showed improvements in score. No gaming parameters decreased. Quality of sleep scores improved slightly.

Overall, the results of the trials represent that combinations of the ingredients in the formulations provided improvements in overall gaming ability of the subjects participating in the trials. The greatest improvements in scores were recorded for memory and recall, mental ability speed, screen vision, finger movement, and energy level, which are all important parameters for effective gaming ability.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

I claim:

1. A sustained release tablet or capsule consisting essentially of caffeine, L-theanine, choline bitartrate, an ashwagandha extract, lutein, zeaxanthin, L-arginine, potassium glycerophosphate, pine bark extract, coconut powder, malic acid, and sugar beet extract.

\* \* \* \* \*

UNITED STATES PATENT AND TRADEMARK OFFICE
CERTIFICATE OF CORRECTION

| | |
|---|---|
| PATENT NO. | : 11,446,305 B2 |
| APPLICATION NO. | : 16/707921 |
| DATED | : September 20, 2022 |
| INVENTOR(S) | : Michael Lelah |

It is certified that error appears in the above-identified patent and that said Letters Patent is hereby corrected as shown below:

On the Title Page

Please change item (73) the Assignee from NutriScience Innovations LLC to Arjuna Natural PVT LTD Signed and Sealed this
Twenty-first Day of March, 2023

Katherine Kelly Vidal
*Director of the United States Patent and Trademark Office*